United States Patent [19]

Yagi et al.

[11] Patent Number: 5,350,677
[45] Date of Patent: Sep. 27, 1994

[54] METHOD OF ASSAYING PHOSPHATASE WITH 3,4-DINITROPHENYLPHOSPHATE

[75] Inventors: Tatsuhiko Yagi; Ryuki Hisada, both of Shizuoka; Hideto Shibata, Yotsukaido, all of Japan

[73] Assignee: Iatron Laboratories, Inc., Tokyo, Japan

[21] Appl. No.: 60,366

[22] Filed: May 11, 1993

Related U.S. Application Data

[60] Division of Ser. No. 971,247, Nov. 3, 1992, which is a continuation of Ser. No. 582,850, Oct. 11, 1990, abandoned.

[30] Foreign Application Priority Data

Feb. 23, 1989 [JP] Japan ................................. 1-41597

[51] Int. Cl.[5] ........................... C12Q 1/42; C07F 9/02
[52] U.S. Cl. ......................................... 435/21; 568/14; 568/15
[58] Field of Search ..................... 435/21; 568/14, 15

[56] References Cited

U.S. PATENT DOCUMENTS 4,754,025  6/1988  Makise et al. ..................... 536/17.7

OTHER PUBLICATIONS

Chlebowski et al. (1976) *J. Biol. Chem*, 251 (4), 1202–1206.
Cook et al. (1983) *J. Gen. Microbiol*, 129 547–555.
Capon et al. (1979) *Bioorg. Chem.*, 8(2), 147–173, in *Chem Abst.*, 92(5), 329, Abst. # 36668.
Megdalow et al. (1982) *J. Biol. Chem.*, 257 (2), 13624–13629.
Sinnott et al. (1978) *Biochem. J.*, 175, 539–546.
Steinmann et al. (1986) *Biopolymers*, 25, 1133–1156.
Komiyama et al. (1989) *J. Chem. Soc. Chem. Comm.*, 24, 1880.
Rossi et al. (1979) *J. Biol. Chem.*, 254(7), 2302–2307.
Hasselbach (1988) *Z. Naturforsch.*, 43C, 929–937.
Stephan et al. (1990) *Eur. J. Biochem.*, 193(2), 535–539.
Stephan et al. (1991) *Eur. J. Biochem.*, 202(2), 551–557.
Caluo (1989) *J. Labelled. Cmpd. Radiopharm.*, XXVII (4), 395–399.
Fernández-Prini et al. (1978) *J. Chem Soc. Faraday Trans I*, 5, 1196–1209.
Ghosh et al. (1986) *Science*, 231, 145–148.
Xu et al. (1991) *Biochemistry*, 30(21), 7788–7796.

*Primary Examiner*—Douglas W. Robinson
*Assistant Examiner*—Jon P. Weber
*Attorney, Agent, or Firm*—Michael N. Meller

[57] ABSTRACT

The substrate, 3,4-dinitrophenylphosphate, has been found to be useful in an assay of acid phosphatase in body fluids.

2 Claims, 1 Drawing Sheet

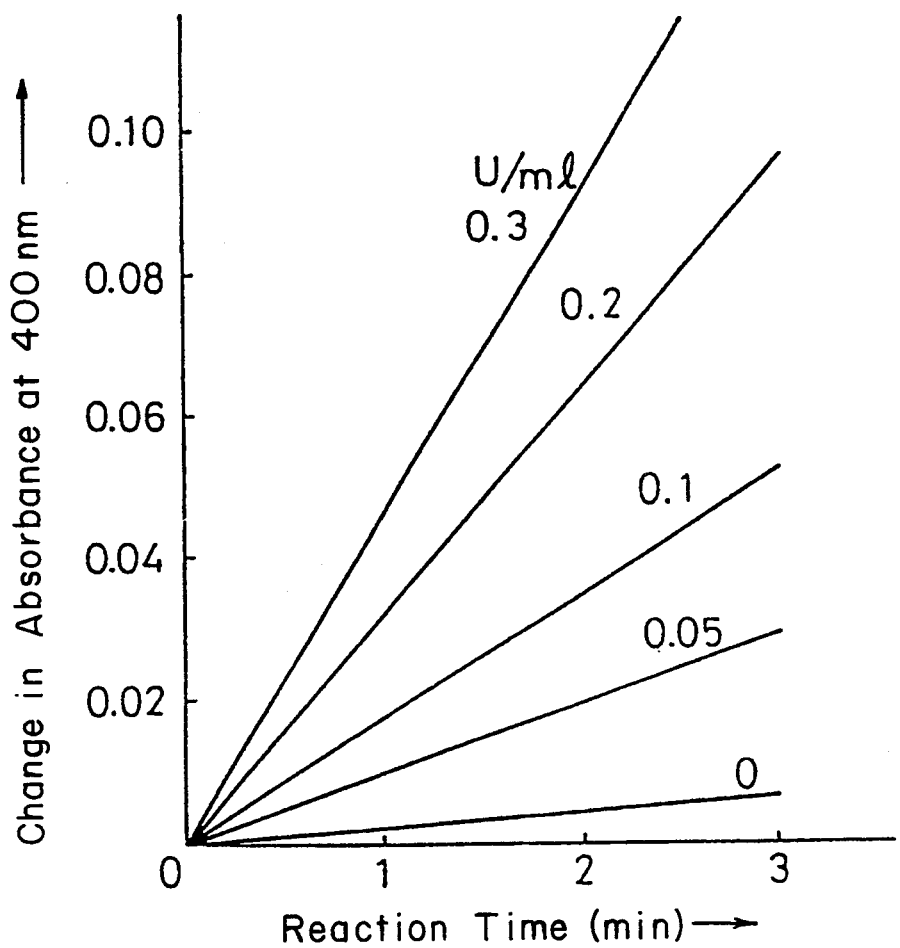
Figure

METHOD OF ASSAYING PHOSPHATASE WITH 3,4-DINITROPHENYLPHOSPHATE

This is a Rule 60 divisional of U.S. patent application Ser. No. 971,247 filed Nov. 3, 1992 which is a file wrapper continuation of U.S. patent application Ser. No. 582,850 filed Oct. 11, 1990 now abandoned.

DESCRIPTION

1. Technical Field

The present invention relates to a substrate for enzyme activity assay, and a method and a reagent for assaying the enzyme activity using the same. More specifically, it relates to a substrate, having a 3,4-dinitrophenoxy group at the end of a molecule, for assaying the activity of N-acetyl-β-D-glucosaminidase or N-acetyl-β-D-hexosaminidase, the activity of alkaline or acidic phosphatase, β-D-glucronidase or β-D-galactosidase, and a method of assaying the above-mentioned enzyme activity by which the indication (absorbance) of the 3,4-dinitrophenol formed from the substrate is measured, and a reagent for assaying the above-mentioned enzyme containing the above-mentioned substrate.

2. Background Art

To carry out an assay of the activity of N-acetyl-β-D-glucosaminidase or N-acetyl-β-D-hexosaminidase (hereinafter abbreviated as NAGase), which are indispensable for an early diagnosis of various kidney diseases such as uriniferous tubule disorders and diabetic kidney disorders, the prior art method uses p-nitrophenyl-N-acetyl-β-D-glucosaminide having a p-nitrophenoxy group at the end of a molecule as the substrate (with p-nitrophenol as a. glycon), and quantitates by colorimetry the p-nitrophenol (aglycon) liberated by the action of the enzyme NAGase at a high pH region (see Method in Enzymology, Vol. 28, p. 772–776). Also, a method is employed in which m-cresol-sulfophthaleinyl-N-acetyl-β-D-glucosaminide is used as the substrate (Japanese Unexamined Patent Publication (Kokai) No. 58-994, Rinsho Byori (Clinical Pathology) XXXI: 2179 (1983)).

Nevertheless, although the optimum pH for NAGase enzyme action is around 5 in the acidic side region, p-nitrophenol and the like do not indicate a required color formation unless in the alkali side region having a pH of 8 or higher. Accordingly, to make an assay of the activity of the enzyme NAGase, in all cases the operations of mixing the enzyme and the substrate to initiate the reaction, stopping the reaction by an addition of an alkali solution after a certain time, and subjecting the reaction mixture to a spectroscopic photometer must be carried out, and thus a drawback arises in that a rate analysis by monitoring under suitable conditions (i.e., rate assay) cannot be performed.

Accordingly, to perform a rate assay, attempts have been made to develop an N-acetyl-β-D-glucosaminide substrate having a compound (aglycon) convertible to p-nitrophenol bound thereto, which forms color at around pH 5 on the acidic side where the action of the NAGase is adequate. For this purpose, the substrates with the following nitro compounds as the aglycon have been proposed (Japanese Unexamined Patent Publication (Kokai) No. 61-177999):

(a) 2,4-dinitrophenol (J. Biol. Chem., Vol. 255, p. 11861–11869, 1980);

(b) 2-chloro-4-nitrophenol (Japanese Unexamined Patent Publication (Kokai) No. 61-112092;

(c) 2,5-dinitrophenol;

(d) 2,6-dichloro-4-nitrophenol;

(e) 2,6-dibromo-4-nitrophenol;

(f) 2,3,6-trichloro-4-nitrophenol;

(g) 2,3,5,6-tetrabromo-4-nitrophenol;

(h) 2,3,5,6-tetrachloro-4-nitrophenol;

(i) 7-sulfo-2,4-dinitro-1-naphthol (Japanese Unexamined Patent Publication (Kokai) No. 61-177999).

Since all of the above compounds have a bulky electron-attracting group substituted at the position adjacent to the phenolic hydroxyl group, to provide the properties of intensifying the acidity and ionization at a low pH to effect a color formation, the substrates having these bound (as aglycon) at the end of a molecule were expected to compensate for the above-mentioned drawback possessed by p-nitrophenol.

Nevertheless, the synthetic substrates obtained by synthesizing these acidic aglycons and N-acetyl-β-D-glucosamine have problems in that they are all difficult to dissolve in water, do not exhibit a satisfactory ionized color formation at a low pH, are per se unstable, and cause problems in enzyme reactions due to the bulky substituents at the 2-position. For example, 2-chloro-4-nitrophenyl-N-acetyl-β-D-glucosaminide is difficult to dissolve in water, and therefore, the substrate cannot be sufficiently dissolved, and thus the procedure of preparing the reagent and the assay accuracy are markedly adversely affected and a satisfactory assay method cannot be obtained for practical application.

Also, a 2,4-dinitrophenyl-N-acetyl-β-D-glucosaminide substrate can be synthesized only with difficulty, and its yield is at most only 5%, even when using a synthetic method considered most suitable as a result of an investigation of various reaction conditions. This is due to the instability of this substance, and the utmost care must be taken to prevent hydrolysis even during the recrystallization at the final stage (supra, J. Biol. Chem., Vol. 255, p. 11861–11869, 1980).

As described above, the problems concerning the substrate of NAGase were not solved by using the various nitrophenol compounds convertible to p-nitrophenol and proposed to date.

The enzymes and substrates thereof to which the state of the art as described above is applicable are shown in Table 1.

TABLE 1

| Enzyme | Substrate |
|---|---|
| N-acetyl-β-D-glucosaminidase (hexosaminidase) | p-nitrophenyl-N-acetyl-β-D-glucosaminide (hexosaminide) |
| α-D-glucosidase | p-nitrophenyl-α-D-glucopyranoside |
| β-D-glucosidase | p-nitrophenyl-β-D-glucopyranoside |
| β-D-galactosidase | o-nitrophenyl-β-D-galactoside |
| phosphatase | p-nitrophenylphosphoric acid |
| β-D-glucronidase | p-nitrophenyl-β-D-glucronide |
| esterase | p-nitrophenylacetic acid |
| allylsulphatase | p-nitrophenylsulfuric acid |

DISCLOSURE OF THE INVENTION

An object of the present invention is to provide a substrate which is sufficiently soluble in water and is stable when used as the substrate for a rate assay of NAGase or phosphatase, β-galactosidase, and β-glucronidase, etc., and further, exhibits an excellent color formability and quantitativity in the acidic pH region, an enzyme activity assay method of assaying an indication (absorbance) of 3,4-dinitrophenol formed from the substrate, and a reagent for use in the enzyme assay using the substrate.

Other objects and advantages of the present invention will be apparent from the following description.

According to the present invention, there is provided a substrate for an assay of N-acetyl-β-D-glucosaminidase or N-acetyl-β-D-hexosaminidase activity, or the activity of alkaline or acidic phosphatase in a living body, and a substrate for an assay of the activity of β-galactosidase or phosphatase to be used as a suitable labelling enzyme, and having a 3,4-dinitrophenoxy group at the end of a molecule.

According to the present invention, there is also provided a method of assaying the activity of N-acetyl-β-D-glucosaminidase or N-acetyl-β-D-hexosaminidase, or an alkaline or acidic phosphatase in a living body, and a method of assaying the β-galactosidase, phosphatase used as the labelling enzyme, which comprises measuring the indication (absorbance) of 3,4-dinitrophenol formed from a substrate having a 3,4-dinitrophenoxy group at the end of a molecule.

According to the present invention, there is further provided a reagent for use in the enzyme assay containing a substrate having a 3,4-dinitrophenoxy group at the end of a molecule.

BRIEF DESCRIPTION OF THE DRAWINGS

FIG. 1 is a graph showing the correlation between the enzyme (NAGase) amount and absorbance change in Example 2.

BEST MODE OF CARRYING OUT THE INVENTION

The present inventors carried out intensive investigations into the electron state of a benzene ring, and the stereospecific reactivity, etc., to obtain a nitrophenol compound instead of the above-described p-nitrophenol, and consequently, found that 3,4-dinitrophenol is suitable for the above-mentioned purpose from the standpoint that it is a derivative having a necessary acidity and does not have a bulky substituent at a position adjacent to the phenolic hydroxyl group, and synthesized various substrates with a 3,4-dinitrophenol bound to the end of a molecule to thereby accomplish the present invention.

The 3,4-dinitrophenol per se to be used in the present invention is a known compound, but no report has been made public about the synthesis of N-acetyl-β-D-glucosaminide, etc., having this compound (bound) at the end of a molecule, and the properties are also unknown. Further, no report at all has been made about the utilization thereof for the substrate for an activity assay of enzymes in a living body, such as NAGase and phosphatase, etc., and the substrate for measuring the activity of a labeled enzyme such as β-D-galactosidase, etc.

The 3,4-dinitrophenol to be used in the present invention is easily dissolved when bound to the end of a substrate molecule, and can be used as the enzyme substrate without the need for a dissolving auxiliary agent. Namely, when 3,4-dinitrophenol is bound to the end of N-acetyl-β-D-glucosaminide, an aqueous solution with a concentration having an extremely high practical applicability of 12 mM can be prepared, but the solution is very stable when stored at low temperatures. In contrast, for example, 2-chloro-4-nitrophenol has an acidity of pk=5.5, but 2-chloro-4-nitrophenyl-N-acetyl-β-D-glucosaminide prepared therefrom is difficult to dissolve, and when introducing same into an assaying kit, a sufficient solubility must be obtained by an addition of a solubilizing auxiliary agent such as cyclodextrin and crown ether, etc., and therefore, the performance thereof as the reagent for the assay is not satisfactory.

By introducing a 3,4-dinitrophenyl group instead of the substrate having a p-nitrophenoxy group, etc., at the end of a molecule, as in the prior art (with p-nitrophenol, etc., as the aglycon), the present invention (i) improves to a great extent the solubility and stability (storability) of the substrate in an aqueous solution of the acting pH of enzyme (neutral or acidic side), and (ii) makes the indication (absorbance measurement) pH of the measurement index substance (3,4-dinitrophenol) derived from of the enzyme reaction identical to or close to the acting pH of enzyme, and thus a correct and precise rate analysis is obtained.

EXAMPLES

The present invention is described with reference to the Examples, but of course the scope of the present invention is not limited to these Examples.

EXAMPLE 1

Synthesis of substrate of NAGase, 3,4-dinitro-phenyl-N-acetyl-β-D-glucosaminide

According to the method of Holleman (Recuil dex Travax Chimiques des Payas-Bas, Vol. 21, p. 432–447, 1902), starting from 20 g of m-nitrophenol, via nitration with conc. nitric acid and separation from the side reaction products, 12 g of a pure 3,4-dinitrophenol was synthesized. The melting point was 134° C., which coincided with the value given in the literature supra.

Then, from 1 g of the 3,4-dinitrophenol synthesized above, a powder of potassium 3,4-dinitrophenolate was prepared and was refluxed together with 2 g of 2-acetamide-2-deoxy-3,4,6-tri-O-acetyl-α-1-chloro-D-glucosaminide in dry acetone for about 3 hours, the acetone was distilled off, the condensed product dissolved in chloroform, and an unreacted substance 3,4-dinitrophenolate removed with a dil. alkali to give 1.5 g of the condensed product, which was purified by recrystallization from ethanol. Finally, the purified condensed product was dissolved in methanol, and deacetylated with a small amount of sodium methylate as the catalyst, to give substantially quantitatively 3,4-dinitrophenyl-N-acetyl-β-D-glucosaminide, which was purified by recrystallization from hot ethanol.

The 3,4-dinitrophenyl-N-acetyl-β-D-glucosaminide (hereinafter also called 3,4-DNG) was found to have sufficient water solubility to be used as the substrate, and an aqueous solution with a concentration of 12 mM sufficient for a NAGase activity assay was easily prepared. Also, the aqueous solution was found to be stable under ice-cooling, with only about a 1% decomposition occurring when left to stand at room temperature overnight, and the decomposition ratio under enzyme reaction conditions (pH 5, 37° C.) for one hour being only 1.5%. The spectrum had a strong absorption at UV-ray 290 nm, but exhibited substantially no absorption at a visible portion 400 nm; and thus was optically remarkably distinguishable.

EXAMPLE 2

Synthesis of 3,4-dinitrophenyl-β-D-galactoside, 3,4-dinitrophenyl-β-D-glucronide and 3,4-dinitro-phenylphosphoric acid, and enzyme reaction Using 3,4-dinitrophenol synthesized according to the same method as in Example 1, and 2,3,4,6-tetra-O-acetyl-α-1-chloro-D-galactoside and 2,3,4-tri-O-acetyl-β-1-chloro-D-glucronide-6-methyl ester, 1.3 g and 0.7 g of the condensed products were obtained, respectively, and after recrystallization from ethanol, deacetylated in the same manner as in Example 1, followed by purification by a recrystallization again from ethanol.

Similarly, 3,4-dinitrophenol was reacted with 2 g of each of $POCl_3$ and $H_3PO_4$ in pyridine, to obtain 1.5 g of the condensed product, which was purified by recrystallization as sodium salt.

Both of the above had solubilities of at least 10 mM, and the respective enzyme activities were assayed with urine and serum as the test samples, using substrates for an activity assay of β-D-galactosidase, β-D-glucronidase, and phosphatase in a 20 mM phosphate buffer (pH 6.5) for galactosidase (derived from E. Coli), and in a 50 mM acetate buffer (pH 5.0) and a 40 mM citrate buffer (pH 5.1) for glucronidase and acidic phosphatase.

EXAMPLE 3

Assay of NAG activity

A reaction mixture containing 1.5 ml of a 0.2M citrate buffer (pH 5) and 1.2 mM of 3,4-DNG (made up to a volume of 3 ml by an addition of an enzyme solution during the reaction) was equilibrated at 37° C., set in a spectrophotometer, and then 100 μl of an NAGase solution (enzyme of human placenta manufactured by Sigma, with activity values according to the standard assay method, Method in Enzymology, Vol. 28, p. 772–776, prepared to 5 kinds of 0, 50 U/liter, 100 U/liter, 200 U/liter and 300 U/liter) was added, and the change with lapse of time of the absorbance at the wavelength of 400 nm was immediately monitored, to obtain the results shown in FIG. 1. A proportional relationship can be seen between the reaction rate corrected with the control, and the enzyme amount, thus indicating that the rate assay was made correctly. The change with a lapse of time of the absorbance without an enzyme addition (control) showed a high reproducibility, and the subsequent assay was continued after once taking the control.

EXAMPLE 4

Assay Method of NAGase using a Reagent Containing 3,4-DNG

| 3,4-DNG | 1.2 mM |
|---|---|
| Citrate buffer (pH 5.0) | 0.1 M |

(2) Operational method

Into 150 μl of a test sample was added 3 ml of the reagent heated at 37° C. for 5 minutes, to carry out the reaction, and the absorbance change at 400 nm per unit time was measured with the reagent blank as a control.

(3) Results

The calibration curve when the standard products were employed exhibited a linearity up to at least 200 U/liter, and the correlation with the 2-chloro-4-nitrophenyl-N-acetyl-β-D-glucosaminide substrate method also was good.

The NAGase activity assay values in living body fluids were as shown in Table 2.

TABLE 2

|  | Method of Invention | 2-CNP-NAG method |
|---|---|---|
| Urine-1 | 5.9 U/liter | 5.2 U/liter |
| Urine-2 | 8.5 U/liter | 8.3 U/liter |
| Urine-3 | 2.8 U/liter | 2.6 U/liter |
| Urine-4 | 10.4 U/liter | 10.0 U/liter |

Note:
2-CNP-NAG method refers to 2-chloro-4-nitrophenyl-N-acetyl-β-D-glucosaminide substrate method.

EXAMPLE 5

Acidic Phosphatase Activity Assay Method

| 3,4-Dinitrophenylphosphoric acid | 10 mM |
|---|---|
| Citrate buffer (pH 5.1) | 40 mM |

(2) Operational method

Into 20 μl of a test sample was added 200 μl of the reagent heated at 37° C. for 5 minutes, to carry out the reaction, and the absorbance change at 400 nm per unit time was measured with the reagent blank as a control.

(3) Results

The calibration curve when the standard products were employed exhibited a linearity up to at least 200 U/liter, and the correlation with the p-nitrophenylphosphoric acid substrate method also was good.

The acidic phosphatase activity assay values in living body fluids were as shown in Table 3.

TABLE 3

|  | Method of Invention | PNP-phosphoric acid method |
|---|---|---|
| Serum-1 | 3.8 U/liter | 3.5 U/liter |
| Serum-2 | 7.2 U/liter | 7.1 U/liter |
| Serum-3 | 14.2 U/liter | 13.5 U/liter |
| Serum-4 | 2.5 U/liter | 2.5 U/liter |

Note:
PNP-phosphoric acid method refers to p-nitrophenylphosphoric acid substrate method

EXAMPLE 6

Comparison of Assay Precision (Prepared as Reagent for Autoanalyzer)

(1) Reagents used (A) 3,4-DNG method (Method of Present Invention)

(1) Preparation of reagent

R-1 Citrate buffer (pH 5.0) 0.1M

R-2 0.1M citrate buffer (pH 5.0) containing 6 mM 3,4-DNG (2) Operational method

After 20 μl of the test sample and 0.4 ml of R-1 were heated at 37° C. for 5 minutes, 0.1 ml of R-2 was added to carry out the reaction, followed by a measurement of the change in absorbance at 400 nm.

(B) 2-Chloro-4-nitrophenyl-N-acetylglucosaminide method

Mayassay NAG-R ® (sold by Sanko Junyaku) was used in accordance with the manufacturer's instructions.

(C) Results (comparison as CV value)

|  | Method A | Method B |
| --- | --- | --- |
| 2 U/liter | 10.8% | 83.4% |
| 51 U/liter | 3.7% | 4.9% |

A great difference appears in the assay precision near the normal value (several U/ml) of NAGase in urine, and the assay results show the advantage of the method of the present invention having an excellent substrate solubility.

The assay reagent compositions in the above examples are general, and various applications are possible for those skilled in the art.

For example, it is possible to conveniently add various surfactants to prevent turbidity in the test sample, to add antiseptics, stabilizers, and further, to add cyclodextrin or various derivatives thereof, for enhancing the color formation sensitivity, relatively reducing the reagent blank value, migrating the 3,4-dinitrophenol pKa value to the acidic side, and increasing the implemented S/N ratio, etc.

EXAMPLE 7

Sensitization Effects with Various Cyclo-Dextrins (CD)

The cyclodextrins (CD) shown below were prepared to a final concentration of 2.4 mM, and the sensitizing effects thereof on 3,4-DNP in a 0.1M citrate buffer (pH 5.0) are shown.

| CD | Sensitization ratio (%) |
| --- | --- |
| No addition | 100 |
| α-CD's | 103–104 |
| β-CD's | 111–146 |
| γ-CD's | 106 |

For β-CD with a high sensitization efficiency, the NAGase is measured based on Example 3, to obtain a similar good sensitization effect.

Particularly, for DEAE(diethylaminoethyl)-β-CD with a high water solubility and high sensitization effect, a 2-fold or higher elevation of the sensitivity is exhibited at a final concentration of 24 mM.

The essence of the present invention resides in substrates having 3,4-dinitrophenol, which is little affected by the pH and temperature and exhibits an excellent solubility as aglycon, and an assay of various enzyme activities by the use thereof, and further, includes the applications described above.

The substrate for an enzyme reaction in a living body, the enzyme activity assay method, and the reagent for use in the assay according to the present invention, as described above, have a particular effect of greatly improving the precision of a rate assay of NAGase and phosphatase, β-D-glucronidase, and β-D-galactosidase.

We claim:

1. A method of assaying an enzyme activity of acidic phosphatase or alkaline phosphatase from a living body comprising:
    allowing a sample to be assayed derived from a living body fluid to react with a substrate solution comprising 3,4-dinitrophenylphosphoric acid or a salt thereof; and
    measuring a color indication of the 3,4-dinitrophenol formed from the substrate.

2. A method of assaying an enzyme activity of acidic phosphatase or alkaline phosphatase from a living body as claimed in claim 1, wherein cyclodextrin is also present in the substrate solution.

* * * * *